United States Patent [19]

Batty, Jr.

[11] Patent Number: 4,613,937

[45] Date of Patent: Sep. 23, 1986

[54] METHOD FOR EXTERNALLY PROGRAMMING A DEVICE IMPLANTED IN A PATIENT

[75] Inventor: John R. Batty, Jr., Miami, Fla.

[73] Assignee: Cordis Corporation, Miami, Fla.

[21] Appl. No.: 582,254

[22] Filed: Feb. 22, 1984

[51] Int. Cl.$^4$ .......................... G06F 15/42; A61N 1/36
[52] U.S. Cl. .................................... 364/413; 364/415; 128/419 P; 128/419 PG
[58] Field of Search .......................... 364/413, 415–417; 128/419 R, 419 P, 419 PG, 419 PS, 419 PT, 420 R, 695–697, 903

[56] References Cited

U.S. PATENT DOCUMENTS

| | | |
|---|---|---|
| 4,146,029 | 3/1979 | Ellinwood, Jr. ............ 128/419 P X |
| 4,164,944 | 8/1979 | Alley, III et al. ........... 128/419 PG |
| 4,166,470 | 9/1979 | Neumann ..................... 128/419 PG |
| 4,231,027 | 10/1980 | Mann et al. ............... 128/419 PT X |
| 4,361,153 | 11/1982 | Slocum et al. ................... 128/419 P |
| 4,365,290 | 12/1982 | Nelms et al. ................. 128/419 P X |
| 4,388,929 | 6/1983 | Renirie et al. ................ 128/419 PG |
| 4,432,360 | 2/1984 | Mumford et al. ............ 128/419 PG |
| 4,441,498 | 4/1984 | Nordling ........................ 128/419 P |
| 4,485,818 | 12/1984 | Leckrone et al. ............ 128/419 PG |
| 4,488,553 | 12/1984 | Nappholz et al. ........... 128/419 PG |

Primary Examiner—Gary V. Harkcom
Attorney, Agent, or Firm—George H. Gerstman

[57] ABSTRACT

A process is provided for programming a device implanted in a patient from an external programming unit. A first access signal is transmitted, from an external source to the implant, to enable a computer within the implant to receive a second access signal. A second access signal is transmitted, from the external source to the implant, to enable the computer to receive and store programming signals representing data. The computer is inhibited from storing the programming signals unless both the first access signal and the second access signal have been received in sequence.

6 Claims, 5 Drawing Figures

METHOD FOR EXTERNALLY PROGRAMMING A DEVICE IMPLANTED IN A PATIENT

CROSS-REFERENCE TO RELATED APPLICATION

This application is related to U.S. Pat. No. 4,550,732.

BACKGROUND OF THE INVENTION

The present invention concerns a novel system for programming a device implanted in a patient from an external programming unit.

Microprocessor-based programmable cardiac pacemakers, which are implanted within the body of a patient, are in wide use today. These pacemakers can be communicated with from an external programmer, to alter the operating parameters of the implanted pacemaker. The pacemakers can be programmed to perform selected operations or to perform a telemetry function by returning information to the external programming device in a selected manner.

Some prior art programmable pacers are communicated with through a serial binary code format. Various transmission methods are used to transmit the binary code, such as magnetic reed switch, ultrasound, infrared signals, radio frequency pulses and bursts, amplitude modulation and frequency modulation.

The proper function of the communication link is of utmost importance to the operation of the pacer and ultimately to the well-being of the patient. There is a concern that the communication link may be affected by improper external sources, such as electromagnetic radiation emitted from various sources including therapeutic equipment. In addition, there may be improper interference from a programming code emitted by a programming device that is not intended to be used with the particular pacer that is implanted in the patient.

Certain prior art units include a reed switch enabling the programming circuit to operate. The reed switch operates as a simple switch which is closed by the application of a magnetic field. The reed switch is in the implant and an external magnet closes the switch to commence the operation. One method of programming is by external magnetic pulsations which force the reed switch to open and close to provide the data signals to the implant circuitry.

In U.S. Pat. No. 4,361,153, assigned to the assignee of the present invention, a system is described in which a carrier signal from the programmer is transmitted to a tank circuit in the implant. The tank circuit reflects back to the external programmer a wave formed with the signal data impressed thereon. The signal data is derived from a microprocessor which is coupled to sensors for various pacer functions such as rate, battery level, etc. If it is desired to change a function of the implanted pacer, the implant tank circuit acts as an antenna and receives the information. Instead of being reflected with signal data that is provided to the tank circuit, it is coupled to the microprocessor for providing the signals to the microprocessor which were received from the external programming circuit for making the desired change.

It is an object of the present invention to provide security so that the signal that is being transmitted from the external source to the implant is the proper signal from the external programming unit rather than some extraneous signal or rather than a signal from an improper programming unit.

BRIEF DESCRIPTION OF THE INVENTION

In accordance with the present invention, a system is provided for programming a device implanted in a patient from an external programming unit. The improvement comprises an implanted device having means for receiving external access signals, means for receiving external programming signals, means for storing the programming corresponding to the external programming signal, means for decoding a first access signal to prevent access to the program storing means unless the first access signal is received, and means for detecting a second access signal to prevent access to the programming storing means unless both the first access signal and the second access signal are received.

In the illustrative embodiment, the implanted device is a cardiac pacer. The means for receiving external access signals comprise an induction coil. The means for receiving external programming signals comprise the programmming input of a microprocessor. The decoding means comprises a binary decoder the input of which is coupled to the means for receiving external access signals and the output of which is coupled to the means for receiving external programming signals.

In the illustrative embodiment, a gate is interposed between the decoder and the means for receiving programming signals. The decoder is operative to enable the gate to transmit the second access signal only if the first access signal has been received.

In the illustrative embodiment, a microprocessor has outputs for operating selective functions, and the microprocessor is operative to inhibit the functions during detection of the second access signal.

In the illustrative embodiment, the decoding means comprises a clocked counter and a sequence detector. The counter is operable to begin running only upon receipt of a signal from the means for receiving external access signals.

In the illustrative embodiment, the external access signals and the external programming signals are generated from the same external unit.

In accordance with the present invention, a process is provided for programming a device implanted in a patient from an external programming unit. The process comprises the steps of transmitting, from an external source to the implant, a first access signal to enable a computer within the implant to receive a second access signal. Thereafter, a second access signal is transmitted, from the external source to the implant, to enable the computer to receive and store programming signals representing data. The computer is inhibited from storing the programming signals unless both the first access signal and the second access signal have been received in sequence. During receipt of the second output signal, selected computer output functions are halted. In the illustrative embodiment, the access signals are digital signals with the second access signal being transmitted at a faster rate than the rate at which the first access signal is transmitted.

A more detailed explanation of the invention is provided in the following description and claims, and is illustrated in the accompanying drawings.

DETAILED DESCRIPTION OF THE ILLUSTRATIVE EMBODIMENT

Figure 1:
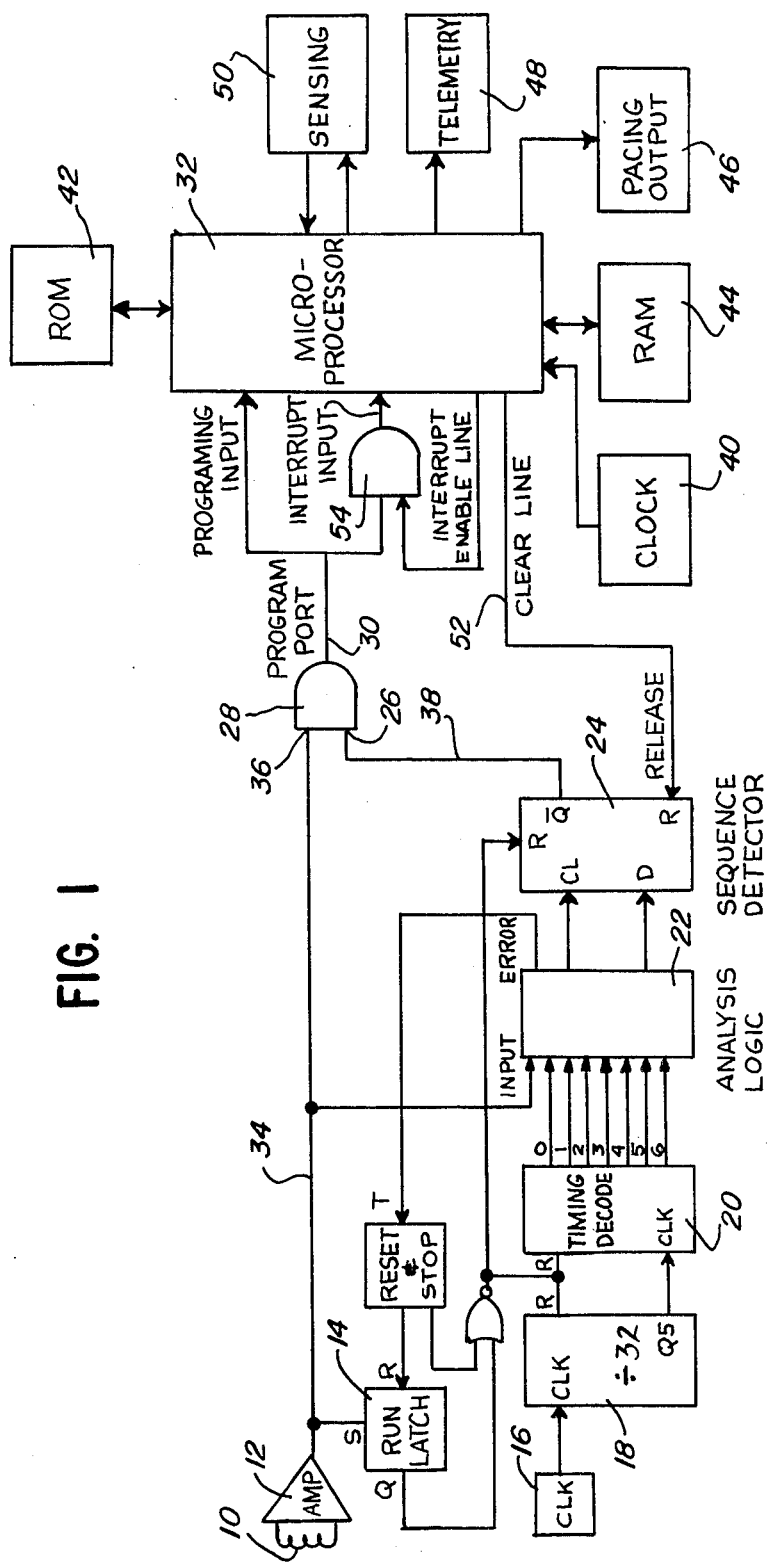
FIG. 1 is a schematic block diagram of the system for programming a device implanted in a patient from an external programming unit, constructed in accordance with the principles of the present invention.

Referring to FIG. 1, a schematic block diagram of the circuitry within the implanted pacer is illustrated therein. Although no limitation is intended, the circuit of the present invention may be fabricated on a CMOS digital logic array chip such as an Advanced Micro-circuits Corporation Q 411 "Quick Chip" with an equivalent gate count of 500. This circuit will operate over the voltage range of 3 to 5 volts at a typical current drain of about one microamp.

As seen in FIG. 1, the pacer's circuitry includes an induction coil 10 for receiving access signals and programming signals from an external programming unit (not shown). The signals are amplified by amplifier 12, integrated and the first edge of the input pulse sets latch 14 to wake up the system. In order to save power, the clock 16, coupled to the clock input of divide by eight counter 18 are normally at rest. The activated clock 16 and counter 18 provide an input to a Johnson counter 20 to provide decoding windows. The decoding windows, which are pulses provided on one of seven output lines depending upon the code, are inputted to an analysis logic circuit 22 which comprises a series of combination and sequential logic elements shown in more detail on FIG. 2. The output of analysis logic circuit 22 is fed to a sequence detector 24, the output of which is fed to an input 26 of transmission AND gate 28. The output 30 of AND gate 28 is connected to the programming input of microprocessor 32. The access signals and the programming signals are fed via line 34 to the other input 36 of AND gate 28.

It can be seen that in order to access the programming input of microprocessor 32, a first proper access code is required. If the sequence detector 24 outputs a high via line 38 to input 26 of AND gate 28, signals on line 34 can be transmitted to the programming input of microprocessor 32. The first access code which is used to access the programming input of microprocessor 32 is transmitted at a relatively slow rate (180 baud). However, once the programming input of microprocessor 32 is accessed, a second access code, which is transmitted at a relatively fast rate (330 baud) is required to achieve operative communication between the programming circuit and the pacer. To this end, a software routine is utilized for analyzing the second access code and for rechecking in order to be certain that the second access code is proper.

The first access code may be referred to as the PAD (program access decoder) code and the second access code may be referred to as the I.D. (identification code). These codes are preferably digital codes in the form of pulse width modulated signals.

Microprocessor 32 is clocked by means of clock 40 which is actually the same clock as clock 16. The program for microprocessor 32 is stored in ROM 42 and microprocessor 32 is coupled to RAMs 44 for temporary storage. The microprocessor has output functions including the pacing output pulse generator 46, telemetry output 48 and sensing function 50, all of which output functions are well known in the art. There is a clear line 52 from microprocessor to sequence detector 24 to clear sequence detector 24 when communication is finished or there has been an error detected. If an error has been detected, microprocessor 32 will clear sequence detector 24 via clear line 52. Since the external programmer will not receive any answer, the person operating the system will know to try again.

Microprocessor 32 normally enables an AND gate 54. However, if the PAD code has been received, i.e., if the first access signal has been received, microprocessor 32 will interrupt its normal output functioning so that it can receive programming information via line 34. It can be seen that it is important that the programming information be transmitted quickly so that the interruption of the microprocessor's output functions is only for a fraction of a second.

Microprocessor 32 controls the sensing hardware and also receives information from the sensing hardware. Microprocessor 32 also controls telemetry circuit 48 for example, by causing the variation in the impedance in the tank coil. Microprocessor 32 also controls the pacing output 46 which includes the rate of fixed stimulation.

Figure 2:
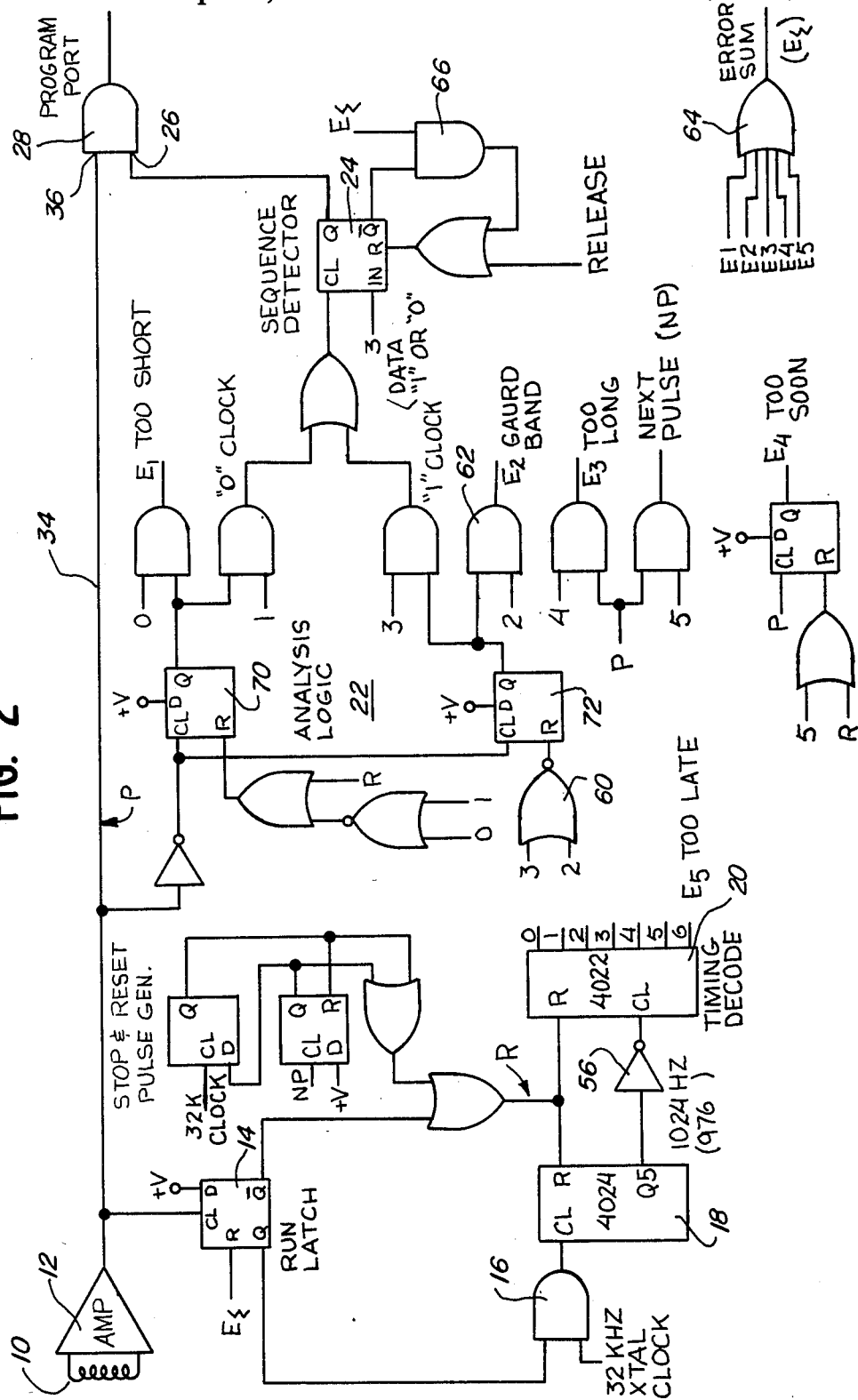
FIG. 2 is a schematic logic diagram of the decoding portion of the circuit of FIG. 1.

A more detailed illustration of the logic circuitry is found in FIG. 2. In FIG. 2, identical reference numerals as in FIG. 1 are used to indicate identical items.

Referring to FIG. 2, it can be seen that clock 16 is outputted to a 4024 divide by thirty-two counter, the output of which is connected through inverter 56 to the clock input of a 4022 Johnson counter. Only seven of the Johnson counter outputs are used. The numbers represent the state provided by the counter outputs, with, for example, counter output 2 being at an input to NOR gate 60 and also at an input to AND gate 62. The number 6 output from Johnson counter 20 is E5 which is fed to the error sum OR gate 64. The output of the error sum OR gate 64 is fed to the reset input of the run latch 14 and also to an input of the AND gate 66 coupled to the sequence detector 24 which is made up of a pair of flip-flops. By noting the numbers at the inputs of the AND gates, OR gates, NOR gates and flip-flops, it can be seen how the corresponding numbered outputs of Johnson counter 20 provide the appropriate windows to form a sequence detector.

Thus the first rising edge of the input data sets the run latch 14 which releases the resets from all counters and latches in the circuit. The run latch allows the counters to time and gate the analysis latch. Divider 18 generates a 1024 hertz (976 microseconds) clock to advance the timing decoder 20 which forms six time slots that the input signal can be checked with for validity and value (0 or 1). Latches 70 and 72 are used to detect the falling edges of input data and decode the conditions E1, 0 E2, or 1. The reset logic to the latches is used to initialize and enable the latches at the appropriate times. The other gates are used to decode the conditions E3, next pulse and E4. All error (E) signals are used to produce the error sum signal. Thus, this circuitry analyzes input pulses and decides whether the pulses will have the proper width (0 or 1) and the proper period. Any error resets the entire system to terminate. As the bits are analyzed, they are inputted to the sequence detector.

After the proper code sequence has been received, all future data is gated to the program port.

Figure 3:
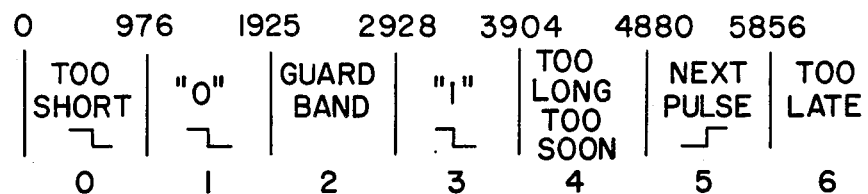
FIG. 3 is a diagram showing the timing windows of the system of FIG. 1.

The timing windows for the system are illustrated in FIG. 3. The numbers at the bottom of FIG. 3 (0 through 6) correspond to the numbers on the output lines of Johnson counter 20. Thus if the pulse drop is seen between 0 and 976 microseconds, thee is an output from the analysis logic 22 indicating error 1 (too short). If the pulse drop is seen between 976 and 1925 microseconds, it is determined to be a "0". If the pulse drop is seen between 2928 microseconds and 3904 microseconds, it is determined to be a "1". If the pulse drop is seen at other times as indicated in FIG. 3, error signals are detected.

Figure 4:
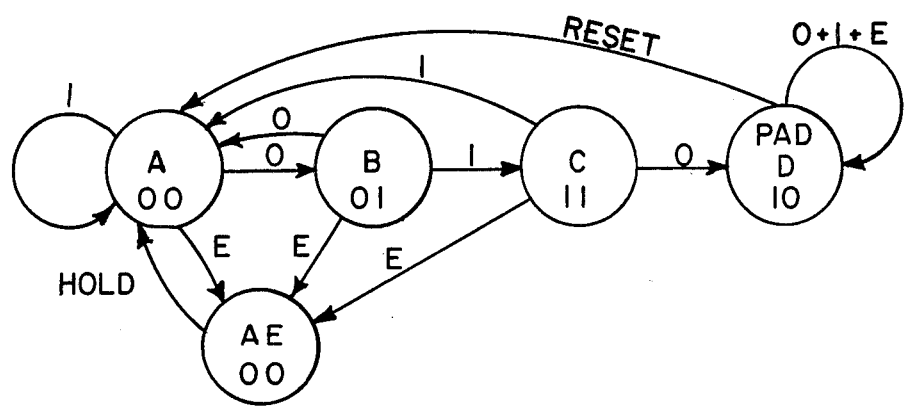
FIG. 4 is a diagram showing the operational states of the sequence detector of FIGS. 1 and 2.

FIG. 4 is the state diagram for the sequence detector for a binary code of 010. Begin at state A. If a zero is received, advance to state B. Thereafter, if a one is received, advance to state C. If a zero is received, advance to state D which unlocks the programming circuit and latches the system so that it awaits the I.D. code for the pacer until it is reset by the microprocessor. It can be seen that if the system is in state B and a zero is received instead of a one, it reverts to state A. Likewise, if the system is in state C and receives a one instead of a zero, it reverts to state A. Once the system reaches state D, a reset signal reverts the system to state A. Hold is the rest position of the system. Invalid timing causes an error signal (E) and the system enters into state AE. Once the system reverts to state A, new data can be entered into the detector.

Figure 5:
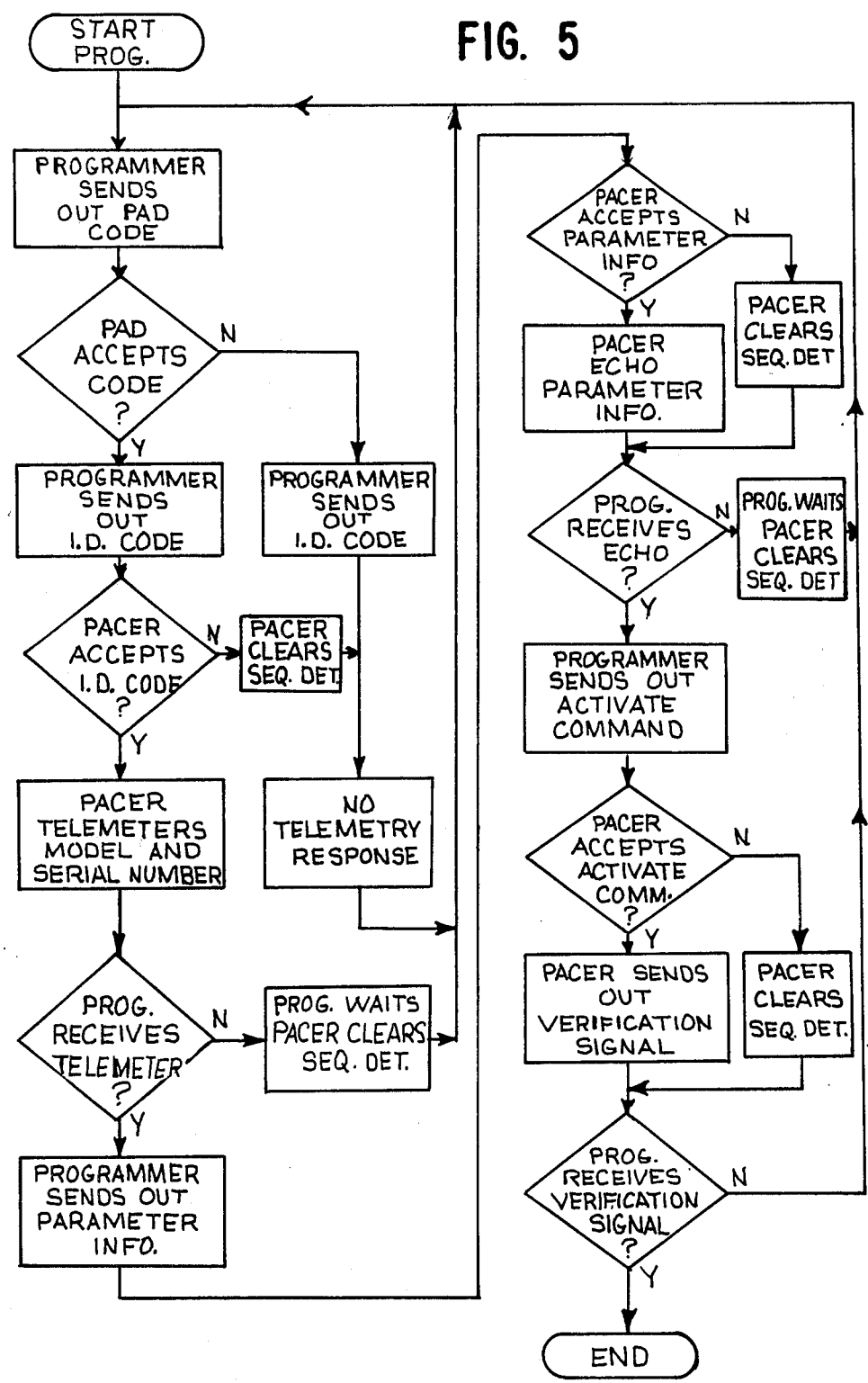
FIG. 5 is a flow chart illustrating the steps of a system in process for programming a device implanted in a patient from an external programming unit, in accordance with the principles of the present invention.

With reference to FIG. 5, a flow chart is provided for illustrating the operation of the system. In use, the user places the external programming unit on the patient's skin above the implanted pacer and looks for a signal indicating that the programming unit in in the proper position. The access code is then transmitted into the implant. First, the programmer sends out the PAD code (the first access code). If this code is correct and accepted, then when the programmer sends out the I.D. code (the second access code) and this code is accepted, the implanted pacer will telemeter the model and serial number back to the programming unit. The programmer will receive the telemetered data and the programmer will send out the parameter information. If the pacer accepts the parameter information, the pacer will echo the parameter information so that the programmer can see that the correct information has been accepted. If the programmer receives the correct echo, the programmer will send out an activate command which will be accepted by the pacer. The pacer can send out a verification signal which is received by the programmer who will know that the commands have been accepted and verified.

If when the programmer sends out the PAD code, it is not accepted, the programmer will send out an I.D. code but there will be no telemetry response. In fact, there will be no telemetry response until both the proper PAD code and I.D. code are accepted by the system.

It can be seen that a system has been provided for programming a device implanted in a patient from an external programming unit, with a security code operating to function as a key to unlock the system. In the illustrative embodiment, a first access code is required to unlock a transmission gate upstream of the microprocessor in the implanted pacer in addition to a software code that is required to unlock the output functioning units, including the pulse generator, sensing circuitry and telemetering circuitry, of the implanted pacer.

Although an illustrative embodiment of the invention has been shown and described, it is to be understood that various modifications and substitutions may be made by those skilled in the art without departing from the novel spirit and scope of the present invention.

What is claimed is:

1. In a process for programming a device implanted in a patient from an external programming unit, the improvement comprising the steps of:

transmitting, from an external source to the implanted device, a first digital access signal to enable a computer within the implanted device to receive a second access signal;

transmitting, from the external source to the implanted device, a second digital access signal to enable the computer to receive and store programming signals representing data;

inhibiting the computer from storing programming signals from the programming unit unless both the first access signal and the second access signal have been received in sequence;

transmitting the second access signal at a faster rate than the rate at which the first access signal is transmitted;

if the first and second access signals have been received in sequence, then transmitting from the implanted device indicia that programming may be commenced;

if the implanted device has transmitted indicia that programming may be commenced, then transmitting program data in digital form from the external programming unit to the computer within the implanted device;

if program data has been received by the computer, then transmitting from the implanted device indicia representing the program data that has been received;

if program data has been received by the computer, then activating selected computer output functions in response to said program data; and if selected functions have been activated, then transmitting from the implanted device verification of such activation.

2. In a process for programming a device implanted in a patient from an external programming unit, the improvement comprising the steps of:

transmitting, from an external source to the implanted device, a first access signal to enable a computer within the implanted device to receive a second access signal;

transmitting, from the external source to the implanted device, a second access signal to enable the computer to receive and store programming signals representing data;

inhibiting the computer from storing programming signals from the programming unit unless both the first access signal and the second access signal have been received in sequence;

if the first and second access signals have been received in sequence, then transmitting from the implanted device indicia that programming may be commenced;

if the implanted device has transmitted indicia that programming may be commenced, then transmitting program data from the external programming unit to the computer within the implanted device;

if program data has been received by the computer, then transmitting from the implanted device indicia representing the program data that has been received.

3. In a process as described in claim 1, wherein said indicia representing the program data that has been received comprises an echo of the program data that has been received.

4. In a process as described in claim 2, wherein said external programming unit includes said external source.

5. In a process as described in claim 2, wherein if the implanted device transmits indicia representing the program data that has been received, then transmitting from the external programming unit an activate commane whereby the programming signals will be stored in the computer; and trnasmitting from the implanted device a verification signal that the programming signals have been stored.

6. In a process for programming a device implanted in a patient from an external programming unit, the improvement comprising the steps of:
- transmitting, from an external source to the implanted device, a first digital access signal to enable a computer within the implanted device to receive a second access signal;
- transmitting, from the external source to the implanted device, a second digital access signal to enable the computer to receive and store programming signals representing data;
- inhibiting the computer from storing programming signals from the programming unit unless both the first access signal and the second access signal have been received in sequence;
- transmitting the second access signal at a faster rate than the rate at which the first access signal is transmitted;
- if the first and second access signals have been received in sequence, then transmitting from the implanted device to the external programming unit, indicia that programming that may be commenced;
- if the implanted device has transmitted indicia that programming may be commenced, then transmitting program data in digital form from the external programming unit to the computer within the implanted device;
- if program data has been received by the computer, then transmitting from the implanted device an echo of the program data that has been received;
- if the correct echo has been received from the implanted device, then transmitting to the implanted device an activate command whereby the program data will be stored in the computer;
- if the activate command has been received by the computer in the implanted device and the program data has been stored, then transmitting from the implanted device a verification signal that the program data has been received and stored.

* * * * *